(12) United States Patent
Sakamoto et al.

(10) Patent No.: US 7,745,669 B2
(45) Date of Patent: *Jun. 29, 2010

(54) PROCESS FOR PRODUCTION OF ALCOHOL COMPOUND

(75) Inventors: Toru Sakamoto, Toyonaka (JP); Shinzo Seko, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/307,223

(22) PCT Filed: Jul. 3, 2007

(86) PCT No.: PCT/JP2007/063289

§ 371 (c)(1),
(2), (4) Date: Dec. 31, 2008

(87) PCT Pub. No.: WO2008/004544

PCT Pub. Date: Jan. 10, 2008

(65) Prior Publication Data

US 2009/0259074 A1 Oct. 15, 2009

(30) Foreign Application Priority Data

Jul. 4, 2006 (JP) ............................. 2006-184254

(51) Int. Cl.
*C07C 33/46* (2006.01)
*C07C 33/28* (2006.01)

(52) U.S. Cl. ...................... 568/715; 568/812; 568/813

(58) Field of Classification Search ................ 568/715, 568/812, 813
See application file for complete search history.

(56) References Cited

U.S. PATENT DOCUMENTS 5,922,880 A 7/1999 Sakamoto et al.

FOREIGN PATENT DOCUMENTS

| EP | 1 221 411 A2 | 7/2002 |
|----|----|----|
| JP | 9-151172 A | 6/1994 |
| JP | 9-504014 A | 4/1997 |
| JP | 2005-325026 A | 11/2005 |
| WO | WO 95/11240 A1 | 4/1995 |
| WO | WO 2004/099145 A2 | 11/2004 |

OTHER PUBLICATIONS

Höger, S. et al., Journal of Organic Chemistry, "High-Yield Macrocyclization via Glaser Coupling of Temporary Covalent Templated Bisacetylenes", 1997, vol. 62, No. 14, pp. 4556-4557.

Niwa et al., "Development of (Phenoxyphenoxy)- and (Benzylphenoxy)propyl Ethers as Potent Insect Juvenile Hormone Mimetics," J. Agric, Food Chem., vol. 37, pp. 462-467, 1989.

Supplementay European Search Report issued on Jan. 14, 2010 in corresponding European Patent Application No. 07 76 8063.

Xi H-T et al., "Synthesis of Unsymmetrical Hydroquinone Ether Chain and Novel Pseudorotaxane,"Journal of Jiangsu Institute of Petrochemical Technology, vol. 13, No. 1, pp. 1-4, Mar. 2001.

*Primary Examiner*—Sikarl A Witherspoon
(74) *Attorney, Agent, or Firm*—Birch, Stewart, Kolasch & Birch, LLP

(57) ABSTRACT

A process for the production of an alcohol compound represented by the formula (3):

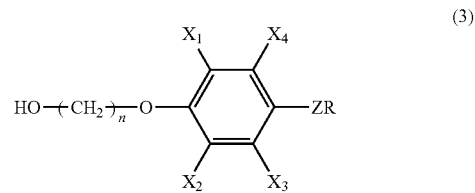

wherein $X_1$, $X_2$, $X_3$, $X_4$, Z, R and n are as defined below, comprising reacting a phenol represented by the formula (1):

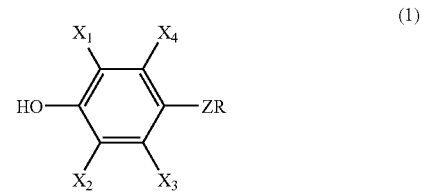

wherein $X_1$, $X_2$, $X_3$ and $X_4$ independently represent a hydrogen atom, a halogen atom or an alkyl group having 1 to 3 carbon atoms; Z represents an oxygen atom or a sulfur atom; and R represents an alkyl group, an alkenyl group, an alkynyl group, or an aralkyl group which may be substituted by a halogen atom, with a haloalcohol represented by the formula (2):

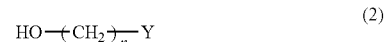

wherein Y represents a chlorine atom or a bromine atom; and n represents an integer of 2 or 3, in a biphase system composed of a water-immiscible organic solvent and an aqueous alkali metal hydroxide solution in the presence of a phase-transfer catalyst.

18 Claims, No Drawings

PROCESS FOR PRODUCTION OF ALCOHOL COMPOUND

TECHNICAL FIELD

The present invention relates to a process for production of an alcohol compound.

BACKGROUND ART

For production of 3-(2,6-dichloro-4-benzyloxy)phenoxy)-1-propyl alcohol, there is a known process which comprises reacting 2-bromo-1-ethanol with 2,6-dichloro-4-benzyloxyphenol in N,N-dimethylformamide in the presence of potassium carbonate to produce 2-(2,6-dichloro-4-benzyloxy)phenoxy)-1-ethanol (Patent Document 1 and Patent Document 2).

Patent Document 1: JP-A 9-151172
Patent Document 2: WO2004-099145A2

DISCLOSURE OF THE INVENTION

Problem to be Solved by the Invention

The above process uses N,N-dimethylformamide as a reaction solvent, and therefore, it has a problem that recovery of the solvent after reaction requires energy or disposal of the solvent after reaction put a burden on the environment. Thus, the present invention is to provide a way to solve the problem.

Means for Solving the Problem

The present invention provides a process for production of an alcohol compound represented by the formula (3):

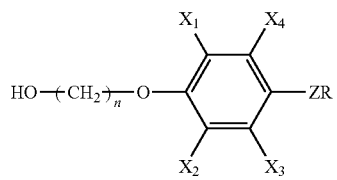

wherein $X_1$, $X_2$, $X_3$ and $X_4$ independently represent a hydrogen atom, a halogen atom or an alkyl group having 1 to 3 carbon atoms, Z represents an oxygen atom or a sulfur atom, R represents an alkyl group, an alkenyl group, an alkynyl group, or an aralkyl group which may be substituted with a halogen atom, and n represents an integer of 2 or 3; which comprises reacting a phenol represented by the formula (1):

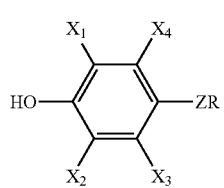

wherein $X_1$, $X_2$, $X_3$, $X_4$, Z and R are as defined above, with a haloalcohol represented by the formula (2):

wherein Y represents a chlorine atom or a bromine atom, and n is as defined above, in a biphase system composed of a water-immiscible organic solvent and an aqueous alkali metal hydroxide solution in the presence of a phase-transfer catalyst.

EFFECTS OF THE INVENTION

According to the process of the present invention, the alcohol compound represented by the formula (3) can be produced efficiently with reduced environmental burdens.

BEST MODE FOR CARRYING OUT THE INVENTION

The present invention will be described below.

Substituents represented by $X_1$, $X_2$, $X_3$ and $X_4$ in the formulae (1) and (3) are described. Examples of the halogen atom represented by $X_1$, $X_2$, $X_3$ or $X_4$ include a fluorine atom, a chlorine atom, a bromine atom and an iodine atom. Examples of the alkyl group having 1 to 3 carbon atoms represented by $X_1$, $X_2$, $X_3$ or $X_4$ include a methyl group, an ethyl group, an n-propyl group, an iso-propyl group and the like. Preferably Z is an oxygen atom.

In the formulae (1) and (3), examples of the alkyl group represented by R include a methyl group, an ethyl group, an n-propyl group, an iso-propyl group, an n-butyl group, a sec-butyl group, a tert-butyl group, an n-pentyl group, an n-hexyl group and the like.

Examples of the alkenyl group include an allyl group. Examples of the alkynyl group include a propargyl group.

Typical examples of the aralkyl group include a benzyl group. Examples of the aralkyl group substituted with a halogen atom include those having benzene rings in which a hydrogen atom is substituted with a fluorine atom, a chlorine atom, a bromine atom or an iodine atom. Specific examples of the aralkyl group substituted with a halogen atom include, but not limited to, a 2-fluorophenylmethyl group, a 3-fluorophenylmethyl group, a 4-fluorophenylmethyl group, a 2-chlorophenylmethyl group, a 3-chlorophenylmethyl group, a 4-chlorophenylmethyl group, a 2-bromophenylmethyl group, a 3-bromophenylmethyl group, a 4-bromophenylmethyl group, a 2-iodophenylmethyl group, a 3-iodophenylmethyl group and a 4-iodophenylmethyl group. In the aralkyl group substituted with a halogen atom, the substitution position of the halogen atom is not specifically limited. Preferably R is an aralkyl group which may be substituted with a halogen atom. More preferably R is a benzyl group.

Examples of the phenol represented by the formula (1) include 4-methoxyphenol, 4-ethoxyphenol, 4-n-propyloxyphenol, 4-iso-propyloxyphenol, 4-n-butyloxyphenol, 4-sec-butyloxyphenol, 4-tert-butyloxyphenol, 4-n-pentyloxyphenol, 4-n-hexyloxyphenol, 4-(2-propenyloxy)phenol, 4-(2-propynyloxy)phenol, 4-benzyloxyphenol, 4-(2-fluorophenylmethyloxy)phenol, 4-(3-fluorophenylmethyloxy)phenol, 4-(4-fluorophenylmethyloxy)phenol, 4-(2-chlorophenylmethyloxy)phenol, 4-(3-chlorophenylmethyloxy)phenol, 4-(4- chlorophenylmethyloxy)phenol, 4-(4-bromophenylmethyloxy)phenol and 4-(4-iodophenylmethyloxy)phenol.

In the formula (2), Y preferably represents a bromine atom and n preferably represents an integer of 3. Examples of the haloalcohol represented by the formula (2) include 2-chloro-1-ethanol, 3-chloro-1-propanol, 2-bromo-1-ethanol and 3-bromo-1-propanol. Preferred is 3-bromo-1-propanol.

Examples of the water-immiscible organic solvent used in the reaction include hydrocarbon compounds. Specific examples thereof include aliphatic hydrocarbon compounds such as hexane and heptane, aromatic hydrocarbon compounds such as toluene, xylene and monochlorobenzene, and their mixtures. Other examples of the water-immiscible organic solvent include chain ether compounds such as diethyl ether and methyl-tert-butyl ether, and their mixtures. As the water-immiscible organic solvent, preferably hydrocarbon compounds or chain ether compounds are used. From the viewpoint of versatility, toluene is more preferably used.

The amount of the water-immiscible organic solvent used is not specifically limited. From the viewpoint of volume efficiency, the amount of the water-immiscible organic solvent used is usually 0.1 parts by weight to 20 parts by weight per 1 part by weight of the phenol represented by the formula (1).

Examples of the aqueous alkali metal hydroxide solution used in the reaction include aqueous solutions of lithium hydroxide, sodium hydroxide and potassium hydroxide. The amount of the alkaline metal hydroxide used is usually 0.9 mol to 3 mol per 1 mol of the phenol represented by the formula (1). The concentration of alkali metal hydroxide in the aqueous alkali metal hydroxide solution is not specifically limited, and is usually 2% by weight to 10% by weight.

Examples of the phase-transfer catalyst include quaternary ammonium salts such as tetra-n-butylammonium chloride, tetra-n-butylammonium bromide, tetra-n-butylammonium iodide, tetra-n-butylammonium sulfate, triethylbenzylammonium chloride and trioctylmethylammonium chloride, quaternary phosphonium salts such as trimethylphenylphosphonium bromide and pyridinium salts such as n-dodecylpyridinium chloride. When the reaction is performed in the presence of such a phase-transfer catalyst, the alcohol compound represented by the formula (3) is produced in good yield. From the viewpoints of availability and versatility, a tetra-n-butylammonium salt such as tetra-n-butylammonium chloride, tetra-n-butylammonium bromide, tetra-n-butylammonium iodide or tetra-n-butylammonium sulfate is preferably used as the phase-transfer catalyst.

The amount of the phase-transfer catalyst used is not specifically limited. Considering economic efficiency and the like, the phase-transfer catalyst is usually used in an amount of 0.01 mol to 0.2 mol per 1 mol of the phenol represented by the formula (1).

The order of mixing the phenol represented by the formula (1), the haloalcohol represented by the formula (2), the water-immiscible organic solvent, the aqueous alkali metal hydroxide solution and the phase-transfer catalyst is not specifically limited. For example, these materials may be mixed all at once and stirred to react. Alternatively, to an aqueous mixture solution of the phenol and the aqueous alkali metal hydroxide solution may be added dropwise a mixture solution of the haloalcohol and the water-immiscible organic solvent. An aqueous mixture solution of the phenol and the aqueous alkali metal hydroxide solution can be also added dropwise to a mixture solution of the haloalcohol and the water-immiscible organic solvent.

The reaction can be performed at a temperature from a room temperature to a refluxing temperature. The reaction temperature is usually from a room temperature to 100° C. From the viewpoint of a reaction rate, the reaction is preferably performed within the range of 50° C. to 100° C. The reaction time is usually about 10 hours to about 20 hours. Progress of the reaction can be monitored by analyzing the residual amount of the phenol represented by the formula (1) using gas chromatography or liquid chromatography.

After the end of the reaction, a reaction mixture is usually allowed to stand and separated to give an oil layer containing the intended product, the alcohol compound represented by the formula (3). The oil layer can be washed with water. The oil layer also can be neutralized with acidic water such as aqueous sulfuric acid, separated, and washed with water again.

After washing, for example, the obtained oil layer can be concentrated under reduced pressure to remove the organic solvent to give a concentrate of the alcohol compound represented by the formula (3). The concentrate can be further subjected to general purification such as silica gel column chromatography, crystallization and recrystallization, if necessary.

As described above, the intended alcohol compound represented by the formula (3) can be produced efficiently in good yield. Examples of the compound represented by the formula (3) include the following compounds.

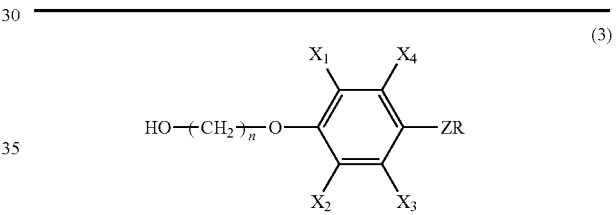

(3)

| No. | n | $X_1$ | $X_2$ | $X_3$ | $X_4$ | Z | R |
|---|---|---|---|---|---|---|---|
| 1  | 2 | H | H  | H | H | O | $CH_3$ |
| 2  | 2 | H | H  | H | H | O | $CH_2CH_3$ |
| 3  | 2 | H | H  | H | H | O | $CH_2CH_2CH_3$ |
| 4  | 2 | H | H  | H | H | O | $CH_2Ph$ |
| 5  | 2 | H | H  | H | H | O | $CH_2CH{=}CH_2$ |
| 6  | 2 | H | H  | H | H | S | $CH_3$ |
| 7  | 2 | H | H  | H | H | S | $CH_2CH_3$ |
| 8  | 2 | H | H  | H | H | S | $CH_2CH_2CH_3$ |
| 9  | 2 | H | H  | H | H | S | $CH_2Ph$ |
| 10 | 2 | H | H  | H | H | S | $CH_2CH{=}CH_2$ |
| 11 | 2 | F | F  | H | H | O | $CH_3$ |
| 12 | 2 | F | F  | H | H | O | $CH_2CH_3$ |
| 13 | 2 | F | F  | H | H | O | $CH_2CH_2CH_3$ |
| 14 | 2 | F | F  | H | H | O | $CH_2Ph$ |
| 15 | 2 | F | F  | H | H | O | $CH_2CH{=}CH_2$ |
| 16 | 2 | F | F  | H | H | S | $CH_3$ |
| 17 | 2 | F | F  | H | H | S | $CH_2CH_3$ |
| 18 | 2 | F | F  | H | H | S | $CH_2CH_2CH_3$ |
| 19 | 2 | F | F  | H | H | S | $CH_2Ph$ |
| 20 | 2 | F | F  | H | H | S | $CH_2CH{=}CH_2$ |
| 21 | 2 | F | Cl | H | H | O | $CH_3$ |
| 22 | 2 | F | Cl | H | H | O | $CH_2CH_3$ |
| 23 | 2 | F | Cl | H | H | O | $CH_2CH_2CH_3$ |
| 24 | 2 | F | Cl | H | H | O | $CH_2Ph$ |
| 25 | 2 | F | Cl | H | H | O | $CH_2CH{=}CH_2$ |
| 26 | 2 | F | Cl | H | H | S | $CH_3$ |
| 27 | 2 | F | Cl | H | H | S | $CH_2CH_3$ |
| 28 | 2 | F | Cl | H | H | S | $CH_2CH_2CH_3$ |
| 29 | 2 | F | Cl | H | H | S | $CH_2Ph$ |
| 30 | 2 | F | Cl | H | H | S | $CH_2CH{=}CH_2$ |
| 31 | 2 | F | Br | H | H | O | $CH_3$ |
| 32 | 2 | F | Br | H | H | O | $CH_2CH_3$ |
| 33 | 2 | F | Br | H | H | O | $CH_2CH_2CH_3$ |

-continued $$HO-(CH_2)_n-O-\underset{\underset{X_2}{|}}{\underset{|}{C_6}}(X_1)(X_4)(X_3)-ZR \quad (3)$$

| No. | n | X₁ | X₂ | X₃ | X₄ | Z | R |
|---|---|---|---|---|---|---|---|
| 34 | 2 | F | Br | H | H | O | CH₂Ph |
| 35 | 2 | F | Br | H | H | O | CH₂CH=CH₂ |
| 36 | 2 | F | Br | H | H | S | CH₃ |
| 37 | 2 | F | Br | H | H | S | CH₂CH₃ |
| 38 | 2 | F | Br | H | H | S | CH₂CH₂CH₃ |
| 39 | 2 | F | Br | H | H | S | CH₂Ph |
| 40 | 2 | F | Br | H | H | S | CH₂CH=CH₂ |
| 41 | 2 | F | CH₃ | H | H | O | CH₃ |
| 42 | 2 | F | CH₃ | H | H | O | CH₂CH₃ |
| 43 | 2 | F | CH₃ | H | H | O | CH₂CH₂CH₃ |
| 44 | 2 | F | CH₃ | H | H | O | CH₂Ph |
| 45 | 2 | F | CH₃ | H | H | O | CH₂CH=CH₂ |
| 46 | 2 | F | CH₃ | H | H | S | CH₃ |
| 47 | 2 | F | CH₃ | H | H | S | CH₂CH₃ |
| 48 | 2 | F | CH₃ | H | H | S | CH₂CH₂CH₃ |
| 49 | 2 | F | CH₃ | H | H | S | CH₂Ph |
| 50 | 2 | F | CH₃ | H | H | S | CH₂CH=CH₂ |
| 51 | 2 | Cl | Cl | H | H | O | CH₃ |
| 52 | 2 | Cl | Cl | H | H | O | CH₂CH₃ |
| 53 | 2 | Cl | Cl | H | H | O | CH₂CH₂CH₃ |
| 54 | 2 | Cl | Cl | H | H | O | CH₂Ph |
| 55 | 2 | Cl | Cl | H | H | O | CH₂CH=CH₂ |
| 56 | 2 | Cl | Cl | H | H | S | CH₃ |
| 57 | 2 | Cl | Cl | H | H | S | CH₂CH₃ |
| 58 | 2 | Cl | Cl | H | H | S | CH₂CH₂CH₃ |
| 59 | 2 | Cl | Cl | H | H | S | CH₂Ph |
| 60 | 2 | Cl | Cl | H | H | S | CH₂CH=CH₂ |
| 61 | 2 | Cl | Br | H | H | O | CH₃ |
| 62 | 2 | Cl | Br | H | H | O | CH₂CH₃ |
| 63 | 2 | Cl | Br | H | H | O | CH₂CH₂CH₃ |
| 64 | 2 | Cl | Br | H | H | O | CH₂Ph |
| 65 | 2 | Cl | Br | H | H | O | CH₂CH=CH₂ |
| 66 | 2 | Cl | Br | H | H | S | CH₃ |
| 67 | 2 | Cl | Br | H | H | S | CH₂CH₃ |
| 68 | 2 | Cl | Br | H | H | S | CH₂CH₂CH₃ |
| 69 | 2 | Cl | Br | H | H | S | CH₂Ph |
| 70 | 2 | Cl | Br | H | H | S | CH₂CH=CH₂ |
| 71 | 2 | Cl | CH₃ | H | H | O | CH₃ |
| 72 | 2 | Cl | CH₃ | H | H | O | CH₂CH₃ |
| 73 | 2 | Cl | CH₃ | H | H | O | CH₂CH₂CH₃ |
| 74 | 2 | Cl | CH₃ | H | H | O | CH₂Ph |
| 75 | 2 | Cl | CH₃ | H | H | O | CH₂CH=CH₂ |
| 76 | 2 | Cl | CH₃ | H | H | S | CH₃ |
| 77 | 2 | Cl | CH₃ | H | H | S | CH₂CH₃ |
| 78 | 2 | Cl | CH₃ | H | H | S | CH₂CH₂CH₃ |
| 79 | 2 | Cl | CH₃ | H | H | S | CH₂Ph |
| 80 | 2 | Cl | CH₃ | H | H | S | CH₂CH=CH₂ |
| 81 | 2 | Br | Br | H | H | O | CH₃ |
| 82 | 2 | Br | Br | H | H | O | CH₂CH₃ |
| 83 | 2 | Br | Br | H | H | O | CH₂CH₂CH₃ |
| 84 | 2 | Br | Br | H | H | O | CH₂Ph |
| 85 | 2 | Br | Br | H | H | O | CH₂CH=CH₂ |
| 86 | 2 | Br | Br | H | H | S | CH₃ |
| 87 | 2 | Br | Br | H | H | S | CH₂CH₃ |
| 88 | 2 | Br | Br | H | H | S | CH₂CH₂CH₃ |
| 89 | 2 | Br | Br | H | H | S | CH₂Ph |
| 90 | 2 | Br | Br | H | H | S | CH₂CH=CH₂ |
| 91 | 2 | Br | CH₃ | H | H | O | CH₃ |
| 92 | 2 | Br | CH₃ | H | H | O | CH₂CH₃ |
| 93 | 2 | Br | CH₃ | H | H | O | CH₂CH₂CH₃ |
| 94 | 2 | Br | CH₃ | H | H | O | CH₂Ph |
| 95 | 2 | Br | CH₃ | H | H | O | CH₂CH=CH₂ |
| 96 | 2 | Br | CH₃ | H | H | S | CH₃ |
| 97 | 2 | Br | CH₃ | H | H | S | CH₂CH₃ |
| 98 | 2 | Br | CH₃ | H | H | S | CH₂CH₂CH₃ |
| 99 | 2 | Br | CH₃ | H | H | S | CH₂Ph |
| 100 | 2 | Br | CH₃ | H | H | S | CH₂CH=CH₂ |
| 101 | 2 | CH₃ | CH₃ | H | H | O | CH₃ |
| 102 | 2 | CH₃ | CH₃ | H | H | O | CH₂CH₃ |
| 103 | 2 | CH₃ | CH₃ | H | H | O | CH₂CH₂CH₃ |
| 104 | 2 | CH₃ | CH₃ | H | H | O | CH₂Ph |
| 105 | 2 | CH₃ | CH₃ | H | H | O | CH₂CH=CH₂ |
| 106 | 2 | CH₃ | CH₃ | H | H | S | CH₃ |
| 107 | 2 | CH₃ | CH₃ | H | H | S | CH₂CH₃ |
| 108 | 2 | CH₃ | CH₃ | H | H | S | CH₂CH₂CH₃ |
| 109 | 2 | CH₃ | CH₃ | H | H | S | CH₂Ph |
| 110 | 2 | CH₃ | CH₃ | H | H | S | CH₂CH=CH₂ |
| 111 | 2 | F | F | F | H | O | CH₃ |
| 112 | 2 | F | F | F | H | O | CH₂CH₃ |
| 113 | 2 | F | F | F | H | O | CH₂CH₂CH₃ |
| 114 | 2 | F | F | F | H | O | CH₂Ph |
| 115 | 2 | F | F | F | H | O | CH₂CH=CH₂ |
| 116 | 2 | F | F | F | H | S | CH₃ |
| 117 | 2 | F | F | F | H | S | CH₂CH₃ |
| 118 | 2 | F | F | F | H | S | CH₂CH₂CH₃ |
| 119 | 2 | F | F | F | H | S | CH₂Ph |
| 120 | 2 | F | F | F | H | S | CH₂CH=CH₂ |
| 121 | 2 | F | F | F | F | O | CH₃ |
| 122 | 2 | F | F | F | F | O | CH₂CH₃ |
| 123 | 2 | F | F | F | F | O | CH₂CH₂CH₃ |
| 124 | 2 | F | F | F | F | O | CH₂Ph |
| 125 | 2 | F | F | F | F | O | CH₂CH=CH₂ |
| 126 | 2 | F | F | F | F | S | CH₃ |
| 127 | 2 | F | F | F | F | S | CH₂CH₃ |
| 128 | 2 | F | F | F | F | S | CH₂CH₂CH₃ |
| 129 | 2 | F | F | F | F | S | CH₂Ph |
| 130 | 2 | F | F | F | F | S | CH₂CH=CH₂ |
| 131 | 2 | Cl | Cl | Cl | H | O | CH₃ |
| 132 | 2 | Cl | Cl | Cl | H | O | CH₂CH₃ |
| 133 | 2 | Cl | Cl | Cl | H | O | CH₂CH₂CH₃ |
| 134 | 2 | Cl | Cl | Cl | H | O | CH₂Ph |
| 135 | 2 | Cl | Cl | Cl | H | O | CH₂CH=CH₂ |
| 136 | 2 | Cl | Cl | Cl | H | S | CH₃ |
| 137 | 2 | Cl | Cl | Cl | H | S | CH₂CH₃ |
| 138 | 2 | Cl | Cl | Cl | H | S | CH₂CH₂CH₃ |
| 139 | 2 | Cl | Cl | Cl | H | S | CH₂Ph |
| 140 | 2 | Cl | Cl | Cl | H | S | CH₂CH=CH₂ |
| 141 | 2 | Cl | Cl | Cl | Cl | O | CH₃ |
| 142 | 2 | Cl | Cl | Cl | Cl | O | CH₂CH₃ |
| 143 | 2 | Cl | Cl | Cl | Cl | O | CH₂CH₂CH₃ |
| 144 | 2 | Cl | Cl | Cl | Cl | O | CH₂Ph |
| 145 | 2 | Cl | Cl | Cl | Cl | O | CH₂CH=CH₂ |
| 146 | 2 | Cl | Cl | Cl | Cl | S | CH₃ |
| 147 | 2 | Cl | Cl | Cl | Cl | S | CH₂CH₃ |
| 148 | 2 | Cl | Cl | Cl | Cl | S | CH₂CH₂CH₃ |
| 149 | 2 | Cl | Cl | Cl | Cl | S | CH₂Ph |
| 150 | 2 | Cl | Cl | Cl | Cl | S | CH₂CH=CH₂ |
| 151 | 3 | H | H | H | H | O | CH₃ |
| 152 | 3 | H | H | H | H | O | CH₂CH₃ |
| 153 | 3 | H | H | H | H | O | CH₂CH₂CH₃ |
| 154 | 3 | H | H | H | H | O | CH₂Ph |
| 155 | 3 | H | H | H | H | O | CH₂CH=CH₂ |
| 156 | 3 | H | H | H | H | S | CH₃ |
| 157 | 3 | H | H | H | H | S | CH₂CH₃ |
| 158 | 3 | H | H | H | H | S | CH₂CH₂CH₃ |
| 159 | 3 | H | H | H | H | S | CH₂Ph |
| 160 | 3 | H | H | H | H | S | CH₂CH=CH₂ |
| 161 | 3 | F | F | H | H | O | CH₃ |
| 162 | 3 | F | F | H | H | O | CH₂CH₃ |
| 163 | 3 | F | F | H | H | O | CH₂CH₂CH₃ |
| 164 | 3 | F | F | H | H | O | CH₂Ph |
| 165 | 3 | F | F | H | H | O | CH₂CH=CH₂ |

-continued $$\text{HO-(CH}_2)_n\text{-O-}\underset{\underset{X_2}{\vert}}{\overset{\overset{X_1}{\vert}}{C_6H_2}}\underset{\underset{X_3}{\vert}}{\overset{\overset{X_4}{\vert}}{}}\text{-ZR} \quad (3)$$

| No. | n | $X_1$ | $X_2$ | $X_3$ | $X_4$ | Z | R |
|---|---|---|---|---|---|---|---|
| 166 | 3 | F | F | H | H | S | $CH_3$ |
| 167 | 3 | F | F | H | H | S | $CH_2CH_3$ |
| 168 | 3 | F | F | H | H | S | $CH_2CH_2CH_3$ |
| 169 | 3 | F | F | H | H | S | $CH_2Ph$ |
| 170 | 3 | F | F | H | H | S | $CH_2CH=CH_2$ |
| 171 | 3 | F | Cl | H | H | O | $CH_3$ |
| 172 | 3 | F | Cl | H | H | O | $CH_2CH_3$ |
| 173 | 3 | F | Cl | H | H | O | $CH_2CH_2CH_3$ |
| 174 | 3 | F | Cl | H | H | O | $CH_2Ph$ |
| 175 | 3 | F | Cl | H | H | O | $CH_2CH=CH_2$ |
| 176 | 3 | F | Cl | H | H | S | $CH_3$ |
| 177 | 3 | F | Cl | H | H | S | $CH_2CH_3$ |
| 178 | 3 | F | Cl | H | H | S | $CH_2CH_2CH_3$ |
| 179 | 3 | F | Cl | H | H | S | $CH_2Ph$ |
| 180 | 3 | F | Cl | H | H | S | $CH_2CH=CH_2$ |
| 181 | 3 | F | Br | H | H | O | $CH_3$ |
| 182 | 3 | F | Br | H | H | O | $CH_2CH_3$ |
| 183 | 3 | F | Br | H | H | O | $CH_2CH_2CH_3$ |
| 184 | 3 | F | Br | H | H | O | $CH_2Ph$ |
| 185 | 3 | F | Br | H | H | O | $CH_2CH=CH_2$ |
| 186 | 3 | F | Br | H | H | S | $CH_3$ |
| 187 | 3 | F | Br | H | H | S | $CH_2CH_3$ |
| 188 | 3 | F | Br | H | H | S | $CH_2CH_2CH_3$ |
| 189 | 3 | F | Br | H | H | S | $CH_2Ph$ |
| 190 | 3 | F | Br | H | H | S | $CH_2CH=CH_2$ |
| 191 | 3 | F | $CH_3$ | H | H | O | $CH_3$ |
| 192 | 3 | F | $CH_3$ | H | H | O | $CH_2CH_3$ |
| 193 | 3 | F | $CH_3$ | H | H | O | $CH_2CH_2CH_3$ |
| 194 | 3 | F | $CH_3$ | H | H | O | $CH_2Ph$ |
| 195 | 3 | F | $CH_3$ | H | H | O | $CH_2CH=CH_2$ |
| 196 | 3 | F | $CH_3$ | H | H | S | $CH_3$ |
| 197 | 3 | F | $CH_3$ | H | H | S | $CH_2CH_3$ |
| 198 | 3 | F | $CH_3$ | H | H | S | $CH_2CH_2CH_3$ |
| 199 | 3 | F | $CH_3$ | H | H | S | $CH_2Ph$ |
| 200 | 3 | F | $CH_3$ | H | H | S | $CH_2CH=CH_2$ |
| 201 | 3 | Cl | Cl | H | H | O | $CH_3$ |
| 202 | 3 | Cl | Cl | H | H | O | $CH_2CH_3$ |
| 203 | 3 | Cl | Cl | H | H | O | $CH_2CH_2CH_3$ |
| 204 | 3 | Cl | Cl | H | H | O | $CH_2Ph$ |
| 205 | 3 | Cl | Cl | H | H | O | $CH_2CH=CH_2$ |
| 206 | 3 | Cl | Cl | H | H | S | $CH_3$ |
| 207 | 3 | Cl | Cl | H | H | S | $CH_2CH_3$ |
| 208 | 3 | Cl | Cl | H | H | S | $CH_2CH_2CH_3$ |
| 209 | 3 | Cl | Cl | H | H | S | $CH_2Ph$ |
| 210 | 3 | Cl | Cl | H | H | S | $CH_2CH=CH_2$ |
| 211 | 3 | Cl | Br | H | H | O | $CH_3$ |
| 212 | 3 | Cl | Br | H | H | O | $CH_2CH_3$ |
| 213 | 3 | Cl | Br | H | H | O | $CH_2CH_2CH_3$ |
| 214 | 3 | Cl | Br | H | H | O | $CH_2Ph$ |
| 215 | 3 | Cl | Br | H | H | O | $CH_2CH=CH_2$ |
| 216 | 3 | Cl | Br | H | H | S | $CH_3$ |
| 217 | 3 | Cl | Br | H | H | S | $CH_2CH_3$ |
| 218 | 3 | Cl | Br | H | H | S | $CH_2CH_2CH_3$ |
| 219 | 3 | Cl | Br | H | H | S | $CH_2Ph$ |
| 220 | 3 | Cl | Br | H | H | S | $CH_2CH=CH_2$ |
| 221 | 3 | Cl | $CH_3$ | H | H | O | $CH_3$ |
| 222 | 3 | Cl | $CH_3$ | H | H | O | $CH_2CH_3$ |
| 223 | 3 | Cl | $CH_3$ | H | H | O | $CH_2CH_2CH_3$ |
| 224 | 3 | Cl | $CH_3$ | H | H | O | $CH_2Ph$ |
| 225 | 3 | Cl | $CH_3$ | H | H | O | $CH_2CH=CH_2$ |
| 226 | 3 | Cl | $CH_3$ | H | H | S | $CH_3$ |
| 227 | 3 | Cl | $CH_3$ | H | H | S | $CH_2CH_3$ |
| 228 | 3 | Cl | $CH_3$ | H | H | S | $CH_2CH_2CH_3$ |
| 229 | 3 | Cl | $CH_3$ | H | H | S | $CH_2Ph$ |
| 230 | 3 | Cl | $CH_3$ | H | H | S | $CH_2CH=CH_2$ |
| 231 | 3 | Br | Br | H | H | O | $CH_3$ |
| 232 | 3 | Br | Br | H | H | O | $CH_2CH_3$ |
| 233 | 3 | Br | Br | H | H | O | $CH_2CH_2CH_3$ |
| 234 | 3 | Br | Br | H | H | O | $CH_2Ph$ |
| 235 | 3 | Br | Br | H | H | O | $CH_2CH=CH_2$ |
| 236 | 3 | Br | Br | H | H | S | $CH_3$ |
| 237 | 3 | Br | Br | H | H | S | $CH_2CH_3$ |
| 238 | 3 | Br | Br | H | H | S | $CH_2CH_2CH_3$ |
| 239 | 3 | Br | Br | H | H | S | $CH_2Ph$ |
| 240 | 3 | Br | Br | H | H | S | $CH_2CH=CH_2$ |
| 241 | 3 | Br | $CH_3$ | H | H | O | $CH_3$ |
| 242 | 3 | Br | $CH_3$ | H | H | O | $CH_2CH_3$ |
| 243 | 3 | Br | $CH_3$ | H | H | O | $CH_2CH_2CH_3$ |
| 244 | 3 | Br | $CH_3$ | H | H | O | $CH_2Ph$ |
| 245 | 3 | Br | $CH_3$ | H | H | O | $CH_2CH=CH_2$ |
| 246 | 3 | Br | $CH_3$ | H | H | S | $CH_3$ |
| 247 | 3 | Br | $CH_3$ | H | H | S | $CH_2CH_3$ |
| 248 | 3 | Br | $CH_3$ | H | H | S | $CH_2CH_2CH_3$ |
| 249 | 3 | Br | $CH_3$ | H | H | S | $CH_2Ph$ |
| 250 | 3 | Br | $CH_3$ | H | H | S | $CH_2CH=CH_2$ |
| 251 | 3 | $CH_3$ | $CH_3$ | H | H | O | $CH_3$ |
| 252 | 3 | $CH_3$ | $CH_3$ | H | H | O | $CH_2CH_3$ |
| 253 | 3 | $CH_3$ | $CH_3$ | H | H | O | $CH_2CH_2CH_3$ |
| 254 | 3 | $CH_3$ | $CH_3$ | H | H | O | $CH_2Ph$ |
| 255 | 3 | $CH_3$ | $CH_3$ | H | H | O | $CH_2CH=CH_2$ |
| 256 | 3 | $CH_3$ | $CH_3$ | H | H | S | $CH_3$ |
| 257 | 3 | $CH_3$ | $CH_3$ | H | H | S | $CH_2CH_3$ |
| 258 | 3 | $CH_3$ | $CH_3$ | H | H | S | $CH_2CH_2CH_3$ |
| 259 | 3 | $CH_3$ | $CH_3$ | H | H | S | $CH_2Ph$ |
| 260 | 3 | $CH_3$ | $CH_3$ | H | H | S | $CH_2CH=CH_2$ |
| 261 | 3 | F | F | F | H | O | $CH_3$ |
| 262 | 3 | F | F | F | H | O | $CH_2CH_3$ |
| 263 | 3 | F | F | F | H | O | $CH_2CH_2CH_3$ |
| 264 | 3 | F | F | F | H | O | $CH_2Ph$ |
| 265 | 3 | F | F | F | H | O | $CH_2CH=CH_2$ |
| 266 | 3 | F | F | F | H | S | $CH_3$ |
| 267 | 3 | F | F | F | H | S | $CH_2CH_3$ |
| 268 | 3 | F | F | F | H | S | $CH_2CH_2CH_3$ |
| 269 | 3 | F | F | F | H | S | $CH_2Ph$ |
| 270 | 3 | F | F | F | H | S | $CH_2CH=CH_2$ |
| 271 | 3 | F | F | F | F | O | $CH_3$ |
| 272 | 3 | F | F | F | F | O | $CH_2CH_3$ |
| 273 | 3 | F | F | F | F | O | $CH_2CH_2CH_3$ |
| 274 | 3 | F | F | F | F | O | $CH_2Ph$ |
| 275 | 3 | F | F | F | F | O | $CH_2CH=CH_2$ |
| 276 | 3 | F | F | F | F | S | $CH_3$ |
| 277 | 3 | F | F | F | F | S | $CH_2CH_3$ |
| 278 | 3 | F | F | F | F | S | $CH_2CH_2CH_3$ |
| 279 | 3 | F | F | F | F | S | $CH_2Ph$ |
| 280 | 3 | F | F | F | F | S | $CH_2CH=CH_2$ |
| 281 | 3 | Cl | Cl | Cl | H | O | $CH_3$ |
| 282 | 3 | Cl | Cl | Cl | H | O | $CH_2CH_3$ |
| 283 | 3 | Cl | Cl | Cl | H | O | $CH_2CH_2CH_3$ |
| 284 | 3 | Cl | Cl | Cl | H | O | $CH_2Ph$ |
| 285 | 3 | Cl | Cl | Cl | H | O | $CH_2CH=CH_2$ |
| 286 | 3 | Cl | Cl | Cl | H | S | $CH_3$ |
| 287 | 3 | Cl | Cl | Cl | H | S | $CH_2CH_3$ |
| 288 | 3 | Cl | Cl | Cl | H | S | $CH_2CH_2CH_3$ |
| 289 | 3 | Cl | Cl | Cl | H | S | $CH_2Ph$ |
| 290 | 3 | Cl | Cl | Cl | H | S | $CH_2CH=CH_2$ |
| 291 | 3 | Cl | Cl | Cl | Cl | O | $CH_3$ |
| 292 | 3 | Cl | Cl | Cl | Cl | O | $CH_2CH_3$ |
| 293 | 3 | Cl | Cl | Cl | Cl | O | $CH_2CH_2CH_3$ |
| 294 | 3 | Cl | Cl | Cl | Cl | O | $CH_2Ph$ |
| 295 | 3 | Cl | Cl | Cl | Cl | O | $CH_2CH=CH_2$ |
| 296 | 3 | Cl | Cl | Cl | Cl | S | $CH_3$ |
| 297 | 3 | Cl | Cl | Cl | Cl | S | $CH_2CH_3$ |

-continued

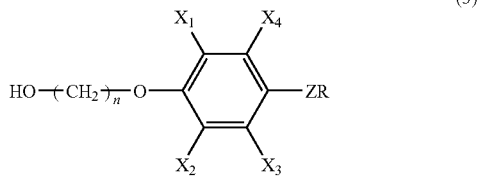

(3)

| No. | n | $X_1$ | $X_2$ | $X_3$ | $X_4$ | Z | R |
|---|---|---|---|---|---|---|---|
| 298 | 3 | Cl | Cl | Cl | Cl | S | $CH_2CH_2CH_3$ |
| 299 | 3 | Cl | Cl | Cl | Cl | S | $CH_2Ph$ |
| 300 | 3 | Cl | Cl | Cl | Cl | S | $CH_2CH=CH_2$ |

EXAMPLE 1

Hereinafter, the present invention will be further described in more detail with reference to Example, which the present invention is not limited to.

EXAMPLE 1

A mixture of 1.15 g of 3-bromopropanol, 7.5 g of toluene and 0.12 g of tetra-n-butylammonium bromide was heated to 60° C., and thereto was added a slurry solution of 1.5 g of 4-(benzyloxy)phenol, 7.5 g of water and 1.22 g of a 27% aqueous sodium hydroxide solution with stirring. After addition, the mixture was stirred at 60° C. for 17 hours. In this period, 0.40 g of 3-bromopropanol and 0.40 g of a 27% aqueous sodium hydroxide solution were further added thereto at the time point of 13 hours. Subsequently, the reaction mixture was cooled to 20° C. After 3.0 g of a 20% aqueous sulfuric acid solution and 15.0 g of toluene were added thereto, the mixture was stirred and then separated. The obtained organic layer was washed with 7.5 g of a 1% aqueous sodium hydroxide solution once and with 7.5 g of water once, and concentrated under reduced pressure to give 2.0 g of 3-(4-benzyloxy)phenoxy)-1-propyl alcohol (purity: 93%, yield: 94%).

INDUSTRIAL APPLICABILITY

According to the process of the present invention, the alcohol compound represented by the formula (3) can be produced efficiently with reduced environmental burdens.

The invention claimed is:

1. A process for production of an alcohol compound represented by the formula (3):

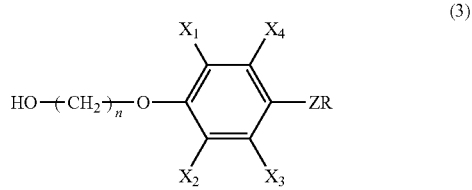

(3)

wherein $X_1$, $X_2$, $X_3$ and $X_4$ independently represent a hydrogen atom, a halogen atom or an alkyl group having 1 to 3 carbon atoms, Z represents an oxygen atom or a sulfur atom, R represents an alkyl group, an alkenyl group, an alkynyl group, or an aralkyl group which may be substituted with a halogen atom, and n represents an integer of 2 or 3; which comprises reacting a phenol represented by the formula (1):

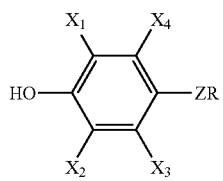

(1)

wherein $X_1$, $X_2$, $X_3$, $X_4$, Z and R are as defined above, with a haloalcohol represented by the formula (2):

(2)

wherein Y represents a chlorine atom or a bromine atom, and n is as defined above, in a biphase system composed of a water-immiscible organic solvent and an aqueous alkali metal hydroxide solution in the presence of a phase-transfer catalyst.

2. The process for production of an alcohol compound according to claim 1, wherein Z is an oxygen atom.

3. The process for production of an alcohol compound according to claim 1 or 2, wherein R is a benzyl group.

4. The process for production of an alcohol compound according to claim 1, wherein the water-immiscible organic solvent is a hydrocarbon compound or a chain ether compound.

5. The process for production of an alcohol compound according to claim 1, wherein the water-immiscible organic solvent is toluene.

6. The process for production of an alcohol compound according to claim 1, wherein a reaction temperature is 50° C. to 100° C.

7. The process for production of an alcohol compound according to claim 1, wherein the phase-transfer catalyst is a tetra-n-butylammonium salt.

8. The process for production of an alcohol compound according to claim 1, wherein the phenol represented by the formula (1) is 2,6-dichloro-4-(benzyloxy)phenol.

9. The process for production of an alcohol compound according to claim 1, wherein n is 3.

10. The process for production of an alcohol compound according to claim 1, wherein the haloalcohol represented by the formula (2) is 3-bromo-1-propanol.

11. The process for production of an alcohol compound according to claim 2, wherein the water-immiscible organic solvent is a hydrocarbon compound or a chain ether compound.

12. The process for production of an alcohol compound according to claim 3, wherein the water-immiscible organic solvent is a hydrocarbon compound or a chain ether compound.

13. The process for production of an alcohol compound according to claim 2, wherein the water-immiscible organic solvent is toluene.

14. The process for production of an alcohol compound according to claim 2, wherein a reaction temperature is 50° C. to 100° C.

15. The process for production of an alcohol compound according to claim 2, wherein the phase-transfer catalyst is a tetra-n-butylammonium salt.

16. The process for production of an alcohol compound according to claim 2, wherein the phenol represented by the formula (1) is 2,6-dichloro-4-(benzyloxy)phenol.

17. The process for production of an alcohol compound according to claim 2, wherein n is 3.

18. The process for production of an alcohol compound according to claim 2, wherein the haloalcohol represented by the formula (2) is 3-bromo-1-propanol.

* * * * *